United States Patent
Krahwinkel et al.

(10) Patent No.: US 9,102,613 B2
(45) Date of Patent: Aug. 11, 2015

(54) METHOD FOR PRODUCING SORBIC ANHYDRIDE AND ALSO USE THEREOF AS A PRESERVATIVE IN FOODS

(75) Inventors: Ralf Krahwinkel, Langenfeld (DE); Robert Markert, Leverkusen (DE); Edwin Ritzer, Leverkusen (DE); Erasmus Vogl, Qingdao (CN)

(73) Assignee: LANXESS DEUTSCHLAND GMBH, Cologne, DE (US)

( * ) Notice: Subject to any disclaimer, the term of this patent is extended or adjusted under 35 U.S.C. 154(b) by 12 days.

(21) Appl. No.: 13/881,850

(22) PCT Filed: Oct. 27, 2011

(86) PCT No.: PCT/EP2011/068860
§ 371 (c)(1),
(2), (4) Date: Dec. 9, 2013

(87) PCT Pub. No.: WO2012/055963
PCT Pub. Date: May 3, 2012

(65) Prior Publication Data
US 2014/0087039 A1    Mar. 27, 2014

(30) Foreign Application Priority Data
Oct. 29, 2010    (EP) ..................................... 10189357

(51) Int. Cl.
*C07C 51/56*    (2006.01)
*A23L 3/3508*    (2006.01)
*A23L 3/3517*    (2006.01)

(52) U.S. Cl.
CPC ............... *C07C 51/56* (2013.01); *A23L 3/3508* (2013.01); *A23L 3/3517* (2013.01); *C07B 2200/09* (2013.01)

(58) Field of Classification Search
CPC combination set(s) only.
See application file for complete search history.

(56) References Cited

U.S. PATENT DOCUMENTS

| | | | |
|---|---|---|---|
| 3,322,825 A | 5/1967 | Fernholz | |
| 3,468,948 A * | 9/1969 | Fernholz et al. | 562/893 |
| 3,547,960 A | 12/1970 | Hauser | |
| 3,607,956 A | 9/1971 | Hornig | |
| 3,639,586 A | 2/1972 | Fernholz | |
| 2004/0062759 A1 | 4/2004 | Abraham et al. | |
| 2009/0264532 A1 | 10/2009 | Kaulen et al. | |
| 2012/0232154 A1 | 9/2012 | Kaulen et al. | |

FOREIGN PATENT DOCUMENTS

| | | |
|---|---|---|
| CN | 101357884 A | 2/2009 |
| GB | 834357 A | 11/1957 |

OTHER PUBLICATIONS

Eckarkt, Cotarca, Phosgenations a Handbook, Wiley-VCH 2003, pp. 353-357.*
European Search Report from co-pending Application EP10189357 dated Jul. 29, 2011, 2 pages.
XP 001525469, Jan. 1, 2003, Toshio Honda et al.

* cited by examiner

*Primary Examiner* — Karl J Puttlitz

(57) ABSTRACT

A method is described for the production of sorbic anhydride, in which alkali metal or alkaline earth metal salts of sorbic acid are reacted with phosgene in an inert organic solvent. In addition, use thereof as a preservative in foods, in particular drinks, is described.

14 Claims, No Drawings

METHOD FOR PRODUCING SORBIC ANHYDRIDE AND ALSO USE THEREOF AS A PRESERVATIVE IN FOODS

The invention relates to a method for the production of sorbic anhydride, and in particular of substantially isomerically pure all-E-sorbic anhydride that is used, inter alia, as a preservative in foods, and also use thereof as a preservative in foods, in particular drinks.

It is known (e.g. from DE-A-102006035202 and WO 2008/014889) that certain anhydrides, e.g. benzoic anhydride, but also benzoic acid and sorbic acid themselves, just like the potassium salts thereof, have preservative properties to foods. It has recently been found in this context that sorbic anhydride has a preservative action about 5 times stronger than, e.g., potassium sorbate. This fact makes sorbic anhydride a very interesting candidate as sterilizer in, e.g., fruit drinks.

If the prior art is searched—with respect to methods for the production of sorbic anhydride—processes are found that firstly describe the production of sorbyl chloride. Production pathways of sorbyl chloride are described proceeding from the polyester of 3-hydroxyhex-4-enoic acid, a preliminary product of sorbic acid production (see AT-A-250928, GB-A-1077739, U.S. Pat. No. 3,322,825, and DE-A-1239681):

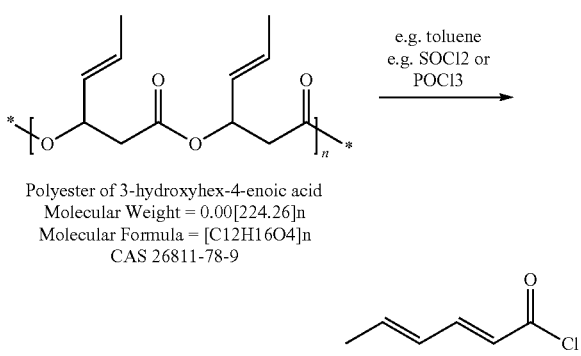

A phosgene-based production of sorbyl chloride may be found in DE-A-1931074:

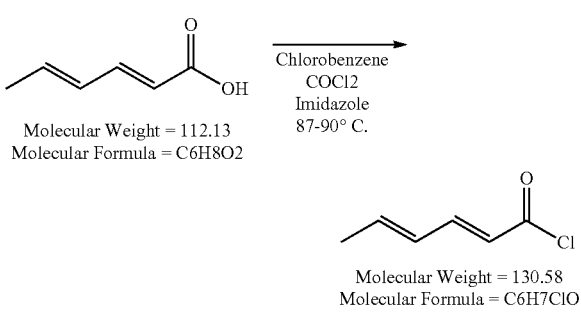

A disadvantage in the above-described variants is, especially, the rapid isomerization of sorbyl chloride under the stated production conditions. In addition to the desired all-E-isomer, approximately 5-20% of further positional isomers are found, e.g. in the case of phosgenation (DE-A-1931074). The isomerization of the all-E-sorbic acid is caused, especially, by the hydrochloric acid liberated in the process and by operating at elevated temperature.

For the polyester cleavage, no empirical values are available on the isomerization. It is in addition tightly bound to the special production method of the polyester and is not everywhere practicable.

In both cases, therefore, it is not the all-E-sorbyl chloride that is arrived at that can serve as starting material for all-E-sorbic anhydride.

Numerous other production methods for sorbyl chloride are supplied by the general chemical literature; in all cases these are chlorinations of sobric acid using thionyl chloride, oxalyl chloride etc., which comprise the same isomerization problems.

For sorbic anhydride itself, only two production pathways may be searched:

1) Production pathways for sorbic anhydride (see in this context DE-A-1283823, GB-A-1138813)

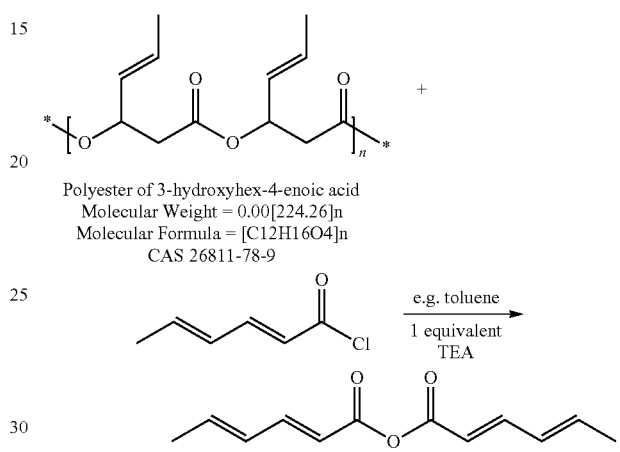

The synthetic pathway has the above-described problems of the polyester and the availability of an all-E-sorbyl chloride.

2) A variant going back to triphosgene may be found in CN-A-101357884 and likewise allows isomerization to be expected owing to the reaction conditions (acid, hot).

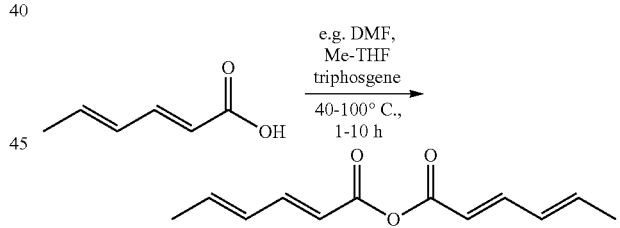

In the literature (Eckarkt, Cotarca, Phosgenations A Handbook, Wiley-VCH 2003, pp. 353-357) there may be found a variant for the production of some symmetrical aliphatic and aromatic anhydrides that are based on the phosgenation of carboxylic acid-triethylammonium salts in inert solvents:

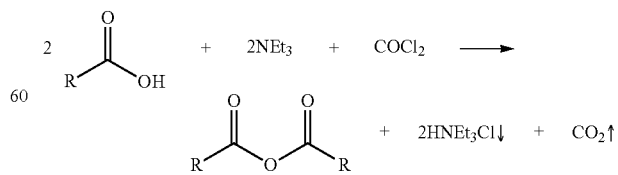

The application of this procedure to the triethylammonium salt of sorbic acid succeeds in principle (see Example 1 (comparative example)), but it has substantial disadvantages. The main disadvantage is the large production of triethylammonium chloride. These must either be separated off (filtered) and then land filled or else recycled. Although an aqueous separation (phase separation after dewatering) is possible, industrially it requires the additional disposal of this wastewater. Also, slight amine traces remaining in the product rapidly lead to darkening and spoilage of the resultant sorbic anhydride.

According to the current prior art, for the production of substantially isomerically pure all-E-sorbic anhydride, no suitable production method can thus be found.

It was the object of the invention to provide a method which is as simple as possible for the production of a substantially isomerically pure all-E-sorbic anhydride.

Surprisingly, it has now been found that the phosgenation of alkali metal or alkaline earth metal salts of sorbic acid (in particular potassium sorbate) in inert solvents succeeds readily and in high yields at suitable temperatures in a one-step synthesis:

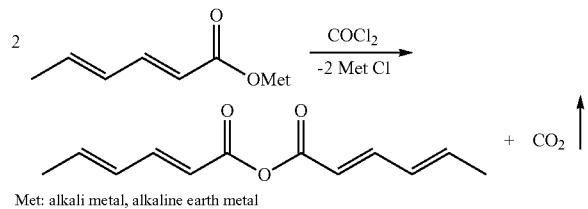

Met: alkali metal, alkaline earth metal

The invention therefore relates to a method for the production of sorbic anhydride, in which alkali metal or alkaline earth metal salts of sorbic acid are reacted with phosgene in an inert organic solvent.

The scope of the invention comprises all of the parameters and explanations situated hereinbefore and stated hereinafter, cited in general or in preferred ranges, among one another, that is to say also between the respective ranges and preferred ranges in any combination.

The expression sorbic acid likewise comprises all stereoisomers of sorbic acid such as, in particular, (2E,4E)-hexa-2,4-dienoic acid, (2Z,4E)-hexa-2,4-dienoic acid, (2E,4Z)-hexa-2,4-dienoic acid and (2Z,4Z)-hexa-2,4-dienoic acid, preferably, sorbic acid is all-E-sorbic acid ((2E,4E)-hexa-2,4-dienoic acid). In the method according to the invention, the desired sorbic anhydride is obtained in high yield and substantially isomerically pure. "Substantially isomerically pure" is taken to mean in this case that the other possible isomers are only formed in an amount in the range of 0.1-0.2 GC peak area %. Preferably, the respective stereoisomers of sorbic anhydride are produced according to the method according to the invention in a purity of 90-95%, particularly preferably in a purity of at least 95%. Particularly preferably, the all-E-sorbic anhydride is produced according to the method according to the invention in a purity of at least 95%.

In the method according to the invention, all alkali metal salts of sorbic acid, such as the lithium, sodium or potassium salt, and also the alkaline earth metal salts of sorbic acid such as the barium or calcium salt can be used. Preference is given to the sodium and potassium salt, particularly preferably the potassium salt, of sorbic acid.

The method according to the invention can be carried out in any usual inert organic solvent as is used for phosgenations. Examples of such solvents are toluene, xylene, chlorobenzene, dichlorobenzene, methyl tert-butyl ether, isoamyl acetate, butyl acetate, ethyl acetate and methyl acetate. Preferably, isoamyl acetate, butyl acetate, ethyl acetate or methyl acetate, particularly preferably ethyl acetate or methyl acetate, is used as solvent.

The reaction temperature is not critical per se and should be in the range between −10 and 50° C., preferably in the range from −5 to 20° C., particularly preferably in the range from 0 to 10° C.

The formation of the sorbic anhydride can be further optimized by the starting stoichiometry, i.e. the ratio of sorbate:phosgene. Usually, this ratio should be in the range from 1:0.4 to 1:0.6. Preferably, the ratio is 1:0.5, particularly preferably 1:0.45.

The reaction time for the phosgenation is in the range from 2 h to 14 h.

The precipitation of the alkali metal or alkaline earth metal chloride formed in molar amounts (e.g. potassium chloride) is not interfering in the method according to the invention and not critical to bodies of water. Therefore, on an industrial scale also, the salt loading can be removed in a simple manner by aqueous phase separation.

It is also surprising that the resultant anhydride is hardly sensitive to the aqueous workup, in such a manner that in the method according to the invention, yields of >90% of theory are obtained (cf. Examples 2 and 3 according to the invention).

Traces of alkali metal chloride or alkaline earth metal chloride such as, e.g., potassium chloride, and traces of sorbic acid in the end product do not interfere with the use as preservative. The method according to the invention is further distinguished in that undesired sorbyl chloride (corrosive and odour nuisance!) is only produced in the range <<0.1%. It may be avoided virtually completely (cf. Example 3 according to the invention) by the selected starting stoichiometry (ratio sorbate:phosgene).

The sequence of addition of sorbates to the phosgene can generally be selected as desired. Preferably, the method according to the invention is carried out in such a manner that the alkali metal or alkaline earth metal salt of sorbic acid is initially charged in a solvent. Preferably, thereafter, the mixture is cooled and then phosgene is introduced. The reaction mixture is worked up according to methods known to those skilled in the art.

The invention further relates to the use of all-E-sorbic anhydride as a preservative for foods, since it has been shown that this isomer has a preservation action approximately five times higher than sorbic acid or sorbate. Preferably, for this purpose, all-E-sorbic anhydride produced by the method according to the invention is used. Preferably, drinks are preserved according to the invention in the preservative doses that are usual per se.

The examples are intended to explain the invention further, but without restricting it in its scope.

EXAMPLES

Example 1

(Comparative Example) Phosgenation of all-E-Sorbic Acid in Ethyl Acetate using Triethylamine as Auxiliary Base In a 1000 ml four-neck flask, equipped with thermometer, intense cooler, submerged tube for phosgene and KPG agitator, 100 g (0.88 mol) of all-E-sorbic acid and 600 g of ethyl acetate are charged. To the resultant suspension are added 101.2 g (1 mol) of triethylamine, whereupon a clear yellow solution forms. The batch was then cooled using a cooling bath to 0-5° C. Then, in the course of 4 hours at 0-5° C., 50.7 g (0.51 mol) of phosgene were introduced, wherein the deposition of the triethylamine hydrochloride is immediately observed. After completion of phosgene metering, the batch was stirred overnight at RT. After examination for freedom from phosgene, the batch was filtered and the suction filter residue was washed with 200 ml of ethyl acetate. The resultant brownish-yellow filtrate was concentrated on a rotary evaporator in a vacuum. The resultant brown oil (90.7 g) was placed under nitrogen into a clear glass bottle and rapidly solidified at room temperature. A GC analysis gave a content of 85.9 weight % of all-E-sorbic anhydride; 9.13 weight % unreacted sorbic acid and 0.31% sorbyl chloride. In $^1$H-NMR, a content of 94.5 weight % anhydride and 2.9 weight % of triethylamine was observed. Isomerization was not observed. Based on the GC content, a yield of 85.6% of theory was determined, based on sorbic acid used.

Example 2

(Example According to the Invention) Phosgenation of the Potassium Sorbate in Ethyl Acetate (Stoichiometry 1:0.5 Equivalent Phosgene)

In a 6 liter ground glass joint reactor equipped with thermometer, intense cooler, immersed tube for phosgene and KPG agitator, 600.87 g of potassium sorbate (4 mol) and 2.4 kg of ethyl acetate were charged. The resultant suspension is cooled to 0-10° C. Then, 197.8 g of phosgene (2 mol) were added within the course of 4 hours. After the introduction, the batch was further stirred overnight without further cooling. After examination for freedom from phosgene, the batch (light-beige suspension) was admixed with 1200 g of deionized water and stirred. After the stirrer was switched off, the lower, aqueous phase was separated off and the upper organic phase was concentrated on the rotary evaporator in vacuum. There remained 410.3 g of a yellow oil, which, after being placed under nitrogen into a clear glass bottle solidified rapidly. The GC analysis of the material gave a content of all-E-sorbic anhydride of 95.8 weight %, in addition to 0.13% isomer, and also 3.3 weight % sorbic acid and 0.64% sorbyl chloride. Based on potassium sorbate used, this is equivalent to a yield of 95.3% of theory.

Example 3

(Example According to the Invention) Phosgenation of Potassium Sorbate in Ethyl Acetate (Stoichiometry 1:0.45 Equivalent of Phosgene)

In a 6 liter ground glass joint reactor equipped with thermometer, intense cooler, immersed tube for phosgene and KPG agitator, 2000 g of potassium sorbate (13.31 mol) and 3.0 kg of ethyl acetate were charged. The resultant suspension is cooled to 0-10° C. Then, 595 g of phosgene (6.02 mol) were introduced in the course of 6 hours. After the introduction, the batch was stirred further overnight without additional cooling. After examination for freedom from phosgene, the batch (light-beige suspension) was sampled. A GC of the reaction mixture showed a content of 28.9 weight % of all-E-sorbic anhydride and 0.03 weight % of sorbyl chloride. Sorbic acid and isomeric anhydride were not detectable.

For the workup, the batch was admixed with 3000 g of deionized water and stirred. After the stirrer was turned off, the lower aqueous phase was separated off and the upper organic phase was concentrated on a rotary evaporator in vacuum. There remained 1154 g of a yellow oil which rapidly solidified after being placed under nitrogen into a clear glass bottle. The GC analysis of the material showed a content of all-E-sorbic anhydride of 95 weight %, in addition to 0.15% isomer, and also 3.6 weight % sorbic acid, and only 0.03% sorbyl chloride. Based on potassium sorbate used, this is equivalent to a yield of 88.7% of theory.

What is claimed is:

1. A method for the production of sorbic anhydride, the method comprising reacting alkali metal saps of sorbic acid and/or alkaline earth metal salts of sorbic acid with phosgene in an inert organic solvent.

2. The method according to claim 1, wherein the sorbic anhydride is all-E-sorbic anhydride and the sorbic acid is (2E,4E)-hexa-2,4-dienoic acid.

3. The method according to either of claims 1 and 2, wherein the alkali metal salt of sorbic acid is potassium sorbate.

4. The method according to claim 1, wherein the inert organic solvent is a solvent selected from the group consisting of toluene, xylene, chlorobenzene, dichlorobenzene, methyl tert-butyl ether, isoamyl acetate, butyl acetate, ethyl acetate and methyl acetate.

5. The method according to claim 1, wherein the reacting is done at a temperature of −10 to 50° C.

6. The method according to claim 1, wherein the alkali metal salts of sorbic acid or the alkaline earth metal salts of sorbic acid are sorbates and the reacting comprises reacting the sorbates with the phosgene at a ratio of sorbate:phosgene of 1:0.6 to 1:0.4 equivalent.

7. The method according to claim 1, wherein the sorbic anhydride produced comprises substantially isomerically pure all-E-sorbic anhydride having a fraction of non all-E-sorbic anhydride isomers of 0.1 to 0.2 GC peak area %.

8. The method according to claim 1, wherein:
the sorbic anhydride is all-E-sorbic anhydride;
the alkali metal salt of sorbic acid is potassium sorbate; and
the inert organic solvent is a solvent selected from the group consisting of toluene, xylene, chlorobenzene, dichlorobenzene, methyl tert-butyl ether, isoamyl acetate, butyl acetate, ethyl acetate and methyl acetate.

9. The method according to cam 8, wherein the reacting is done at a temperature of −5° C. to 20° C.

10. The method according to claim 8, wherein the reacting is done at a temperature of 0° C. to 10° C.

11. The method according to claim 9, wherein the reacting comprises reacting the potassium sorbate with the phosgene at a ratio of sorbate:phosgene of 1:0.6 to 1:0.4 equivalent.

12. The method according to claim 11, wherein the ratio is 1:0.5 equivalent.

13. The method according to claim 11, wherein the ratio is 1:0.45 equivalent.

14. The method according to claim 1, wherein;
the alkali metal salt of sorbic acid is potassium sorbate;
the reacting comprises reacting the potassium sorbate with the phosgene at a ratio of sorbate:phosgene of 1:0.45 equivalent and a temperature of 0° C. to 10° C.; and
the sorbic anhydride produced comprises substantially isomerically pure all-E-sorbic anhydride having a fraction of non all-E-sorbic anhydride isomers of 0.1 to 0.2 GC peak area %.

* * * * *